(12) United States Patent
Liversidge

(10) Patent No.: US 10,058,660 B2
(45) Date of Patent: Aug. 28, 2018

(54) NEEDLE SAFETY DEVICES

(75) Inventor: Barry Peter Liversidge, Colchester (GB)

(73) Assignee: Tip-Top.Com LTD (GB)

( * ) Notice: Subject to any disclaimer, the term of this patent is extended or adjusted under 35 U.S.C. 154(b) by 155 days.

(21) Appl. No.: 13/640,142

(22) PCT Filed: Apr. 21, 2011

(86) PCT No.: PCT/GB2011/050807
§ 371 (c)(1),
(2), (4) Date: Oct. 9, 2012

(87) PCT Pub. No.: WO2011/131997
PCT Pub. Date: Oct. 27, 2011

(65) Prior Publication Data
US 2013/0035646 A1 Feb. 7, 2013

(30) Foreign Application Priority Data

Apr. 23, 2010 (GB) .................................. 1006789.0
Jun. 1, 2010 (GB) .................................. 1009069.4

(51) Int. Cl.
*A61M 5/32* (2006.01)
*A61M 5/50* (2006.01)
*A61M 5/31* (2006.01)

(52) U.S. Cl.
CPC ......... *A61M 5/3202* (2013.01); *A61M 5/3204* (2013.01); *A61M 5/5086* (2013.01);
(Continued)

(58) Field of Classification Search
CPC .... A61M 5/32; A61M 5/3202; A61M 5/3204; A61M 5/5086; A61M 2005/319;
(Continued)

(56) References Cited

U.S. PATENT DOCUMENTS 4,474,734 A * 10/1984 Cooper ........................... 422/31
4,938,745 A *  7/1990 Sagstetter ..................... 604/263
(Continued)

FOREIGN PATENT DOCUMENTS

WO         9748430       12/1997
WO       2009040601       4/2009
(Continued)

OTHER PUBLICATIONS

International Search Report, PCT International Application No. PCT/GB2011/050807, dated Oct. 5, 2011.

*Primary Examiner* — Kevin C Sirmons
*Assistant Examiner* — Leah Swanson
(74) *Attorney, Agent, or Firm* — Grossman Tucker Perreault & Pfleger PLLC

(57) ABSTRACT

A safety device for a medical injector supporting a needle projecting forwardly from the front of the injector has a tubular sleeve slidable rearwardly to expose at least the tip of a supported needle. The sleeve has a forward end for contacting an injection site and a removable cover for the needle is attached to the forward end of the sleeve. The sleeve has an external end face lying in a radial plane and having an orifice through which a needle projects when the sleeve slides rearwardly. The removable cover effects a seal to the forward end of the sleeve. Alternatively, the cover may frictionally engage the forward end of the sleeve or the cover may have a bore into which an enlargement member may be pressed so as to expand the cover within the sleeve and connect the cover to the sleeve.

20 Claims, 10 Drawing Sheets

(52) U.S. Cl.
CPC .................. *A61M 2005/312* (2013.01); *A61M 2005/3109* (2013.01)

(58) Field of Classification Search
CPC .............. A61M 2005/312; A61M 5/50; A61M 5/3243; A61M 2005/3103; A61M 2005/3107; A61M 2005/3109; A61M 2005/3104; A61M 2005/3247; A61M 2005/325; A61M 39/20; A61M 2039/0288
USPC ................ 604/198, 110, 192, 136, 137, 111, 604/164.08, 197, 256, 263
See application file for complete search history.

(56) References Cited

U.S. PATENT DOCUMENTS

| | | | | |
|---|---|---|---|---|
| 5,104,379 | A * | 4/1992 | Nakamura | A61B 1/00062 604/111 |
| 5,273,542 | A * | 12/1993 | Blake, III | 604/110 |
| 5,549,708 | A * | 8/1996 | Thorne et al. | 604/110 |
| 5,616,135 | A | 4/1997 | Thorne et al. | |
| 6,077,247 | A * | 6/2000 | Marshall | A61M 5/2033 604/135 |
| 6,196,998 | B1 * | 3/2001 | Jansen | A61M 5/3134 604/111 |
| 7,374,555 | B2 * | 5/2008 | Heinz et al. | 604/111 |
| 2002/0193737 | A1 * | 12/2002 | Popovsky | A61M 5/326 604/110 |
| 2003/0040715 | A1 * | 2/2003 | D'Antonio et al. | 604/187 |
| 2011/0034879 | A1 * | 2/2011 | Crow | A61M 5/2033 604/197 |
| 2013/0030365 | A1 * | 1/2013 | Liversidge | 604/111 |

FOREIGN PATENT DOCUMENTS

| | | |
|---|---|---|
| WO | 2009081133 | 7/2009 |
| WO | 2009155277 | 12/2009 |
| WO | 2010094916 | 8/2010 |

* cited by examiner

NEEDLE SAFETY DEVICES

CROSS REFERENCE TO RELATED APPLICATION

The present application is the U.S. national stage application of International Application PCT/GB2011/050807, filed Apr. 21, 2011, which international application was published on Oct. 27, 2011 as International Publication WO 2011/131997. The International Application claims priority of British Patent Application 1006789.0 filed on Apr. 23, 2010 and 1009069.4, filed on Jun. 1, 2010.

This invention concerns safety devices for medical injectors supporting a needle projecting forwardly from the front of the injector body. In particular, this invention relates to several different cover arrangements for needle safety devices as aforesaid.

In particular, but not exclusively, this invention relates to improvements in the soft cover for a medical needle associated with a safety device such as has been disclosed in my earlier UK Patent Application No. 10 01506.3, filed 1 Feb. 2010. Further, in its preferred aspects, this invention relates to improvements in the soft cover arrangements described in my earlier UK Patent Applications Nos. 10 02327.3 filed on 11 Feb. 2010 and 10 06789.0 filed on 23 Apr. 2010. All these applications will hereinafter be referred to as "said applications".

The needle safety device of this invention is intended for use with a medical injector supporting a needle used to penetrate a human or animal body, or for other medical uses such as the penetration of a pierceable membrane of an intravenous medication system. In the following, all medical uses of the safety device will be described simply as the penetration of a body, even though specific embodiments may be intended for other medical uses.

Throughout this specification the terms "forward" and "forwardly" used in relation to the safety device and an injector for use therewith refer to those ends of the components which are approached to a body when a procedure is to be performed, and the direction towards those ends. Conversely, the terms "rearward" and "rearwardly" refer to those ends of the components opposed to the forward ends and the direction away from those forward ends.

Needle safety devices are being increasingly used with medical injectors, to confer either passive or active safety on the needle. Such a device frequently has a sleeve which is slidable with respect to the injector or syringe, such that the needle is exposed by rearward sliding movement of the sleeve relative to the injector or syringe and subsequent to the performance of an injection, the sleeve slides forwardly once more again to confer protection to the needle. With many such devices, the sleeve is locked in its forward position following the performance of an injection, so that the needle cannot be re-used.

It is the conventional practice with a needle safety device as described above to provide a cover for the needle and which engages the needle hub or part of the syringe which mounts the needle. Such a cover is applied either in a sterile environment or during a sterilising procedure in the course of the manufacture of the device so that sterility of the needle itself is assured, up to the point at which the cover is pulled away to expose the needle ready for use. In the case of a pre-filled syringe having a needle permanently fitted thereto, the cover will also serve as a stopper for the needle, to prevent leakage of the drug out of the sharp tip of the needle. Such a cover is of a soft resilient rubber or a similar elastomeric material to allow the creation of a seal at the rearward end of the cover against the needle hub or the injector or syringe and also to allow the needle tip to penetrate the material of the cover without damaging the needle tip.

The manufacture of a syringe or other injector is a highly automated process performed under sterile conditions. In the case of a syringe having a staked-in needle, the soft needle cover can be applied to the syringe before sterilisation of the finished product has been completed. A major problem in this manufacturing process is that the cover pops off the end of the syringe and needle in the course of the sterilisation process due to pressure changes in the sterilisation process and if this occurs, the syringe must be discarded. In the course of a fully automated process, this leads to complications and possible delays in the manufacturing process.

It is an aim of this invention to propose various cover arrangements for a syringe or other injector fitted with a safety needle device in the course of the manufacture of the syringe. Embodiments of different aspects of this invention include a soft cover for the needle and which permits the needle itself to remain sterile following manufacture, or, in the case of a syringe which is to be subsequently pre-filled with a drug, the cover also stops (i.e. closes off) the sharp tip of the needle to prevent drug leakage therefrom following pre-filling, or which maintains clean or perhaps even sterile the forward end of a protecting sleeve of the safety needle device which is likely to come in contact with the skin of a patient.

According to this invention, there is provided a needle safety device for a medical injector supporting a needle projecting forwardly from the front of the injector body, which device comprises a tubular sleeve for a supported needle and slidable rearwardly with respect thereto to expose at least the tip of the supported needle, the sleeve having a forward end for contacting an injection site, and a removable cover for the needle, wherein the needle safety device is arranged in accordance with one or more of the following features:

(1) The cover is attached to said forward end of the sleeve, in sealing contact therewith. For example, the cover may be attached to the forward end of the sleeve by an adhesive or by one of a thermal or chemical fusing, welding or moulding operation. Conveniently, the attachment may be performed by a laser fusing or welding operation and in this case the welding operation may be performed from within the sleeve.

In an alternative process, the cover is attached to the forward end of the sleeve by one of a co-moulding operation or an insert moulding operation (both well known and understood in the plastics moulding art) thereby forming the cover integrally with but separable from the sleeve.

With any of the above arrangements, the forward end of the sleeve may define an external end face lying substantially in a radial plane relative to the sleeve, there being an orifice in said end face through which the needle projects when the sleeve is slid rearwardly. The removable cover may be attached to and effect a seal to said external end face, thereby to ensure that the end face may remain sufficiently clean until the cover is removed, immediately prior to use of the injector to perform a medical procedure. In this case, removal of the cover may be effected by separating or breaking away the attachment. In the alternative, the cover may be separable into two parts about a generally radial plane, such that removal of the major part of the cover leaves a minor part still attached to the external end face of the sleeve.

(2) The forward end of the sleeve has an orifice through which, in use, the needle projects. The cover extends through said orifice and frictionally engages the forward end of the sleeve around said orifice thereby to connect the cover to the forward end of the sleeve. The frictional engagement may take place between a cylindrical wall of the sleeve at the forward end thereof and an external surface of the cover.

Preferably, the forward end of the sleeve defines an external end face lying substantially in a radial plane relative to the sleeve, the orifice being provided in that external end face so that the needle projects therethrough when the sleeve is slid rearwardly. In this case, the removable cover may have a surface which engages and effects a seal to said end face.

(3) The forward end of the sleeve has an orifice through which the needle projects and the cover extends through said orifice, and the cover has an opening extending axially from the end of the cover externally of the sleeve into a part of the cover within the sleeve, there being an enlargement member pressed into said opening in the cover so as to lie within the sleeve thereby to expand the cover within the sleeve and effect a connection therebetween. With this arrangement, the cover advantageously is resiliently deformable though it would be possible to have a cover of a plastically deformable material such that the cover remains expanded, once the enlargement member has been pressed into said opening.

A separate element such as a ball may be forced along the opening in the cover to pass through the orifice in the sleeve such that the region of the cover within the sleeve is expanded by the presence of the element in the opening. In an alternative arrangement, the separate element is in the form of a plunger having a rounded head at one end and a grip at the other end, whereby pressure on the grip in the axial direction towards the rear end of the cover forces the head deeper into the opening and when so located, a pull on the grip in the axial direction away from the rear end of the cover draws the plunger together with the cover out of the sleeve, so preparing the device ready for use.

Either the second or third arrangements may be arranged to embody the concept described and claimed in my earlier Application No. 10 06789.0. Thus, the forward end of the sleeve may define an external end face lying substantially in a radial plane relative to the sleeve and the orifice is provided in the end face so that the needle projects therethrough when the sleeve is slid rearwardly. For this arrangement, the removable cover has a surface which engages and effects a seal to the end face, so that the end face may remain sterile until the cover is removed.

(4) The forward end of the cover is provided with a tab connected to the main part of the cover by a web which holds the tab in a generally radial plane with respect to the axis of the sleeve, whereby the tab is freed for use to pull the cover away from the sleeve by dividing the web so allowing the tab to flex out of said generally radial plane.

The web may be separable by tearing with the application of a sufficient force on the tab to effect said flexing movement thereof, which preferably takes place about a connection to the cover at one end of the tab adjacent a side wall of the cover. In this case, the web may extend across the cover in a generally diametral direction. Conveniently, the tab is connected to the main part of the cover by a "live" hinge defined by a weakened zone of the material of the cover and tab.

(5) The forward end of the sleeve has an orifice through which the needle projects and a resilient cover extends through said orifice, the cover having a external tubular part which overlies an external portion of the sleeve extending rearwardly from the forward end thereof. Advantageously, the cover tubular part can be inverted by the resilient deformation thereof so as to project forwardly from the forward end of the sleeve and serve as a grip for subsequent pulling of the cover axially away from the sleeve.

The external tubular part of the cover may be a close resilient fit on the external portion of the sleeve to effect a seal thereto, and so also to seal the forward end face of the sleeve. The resilient fit on the external portion of the sleeve may additionally serve to prevent inadvertent removal of the cover.

Any of the above arrangements of this invention may include the features of my earlier Patent Application No. 10 02327.3. As such, a first part of the cover may be disposed within the sleeve so that a second part of the cover is external to the sleeve, the first part of the cover effecting a seal to at least the tip of the needle and the second part of the cover being manually-grippable for pulling the cover away from the device.

The first part of the cover may have a rear end engaging a needle hub supporting the needle and the first part is maintained under compression within the sleeve so as to effect a seal to the needle hub.

Also, many of the embodiments may be able to provide tamper-evidence, to show if the cover has been pulled away and then replaced.

This invention extends to a safety device of this invention as described above in combination with a medical needle, the removable cover of the device covering the needle until that cover is removed. Further, the invention extends to a safety device of this invention in combination with a medical injector wherein the needle projects forwardly from the body of the injector and the safety device co-operating with that injector.

By way of example only, specific embodiments of the several different arrangements of this invention will now be described in detail, reference being made to the accompanying drawings in which:—

Figure 1:
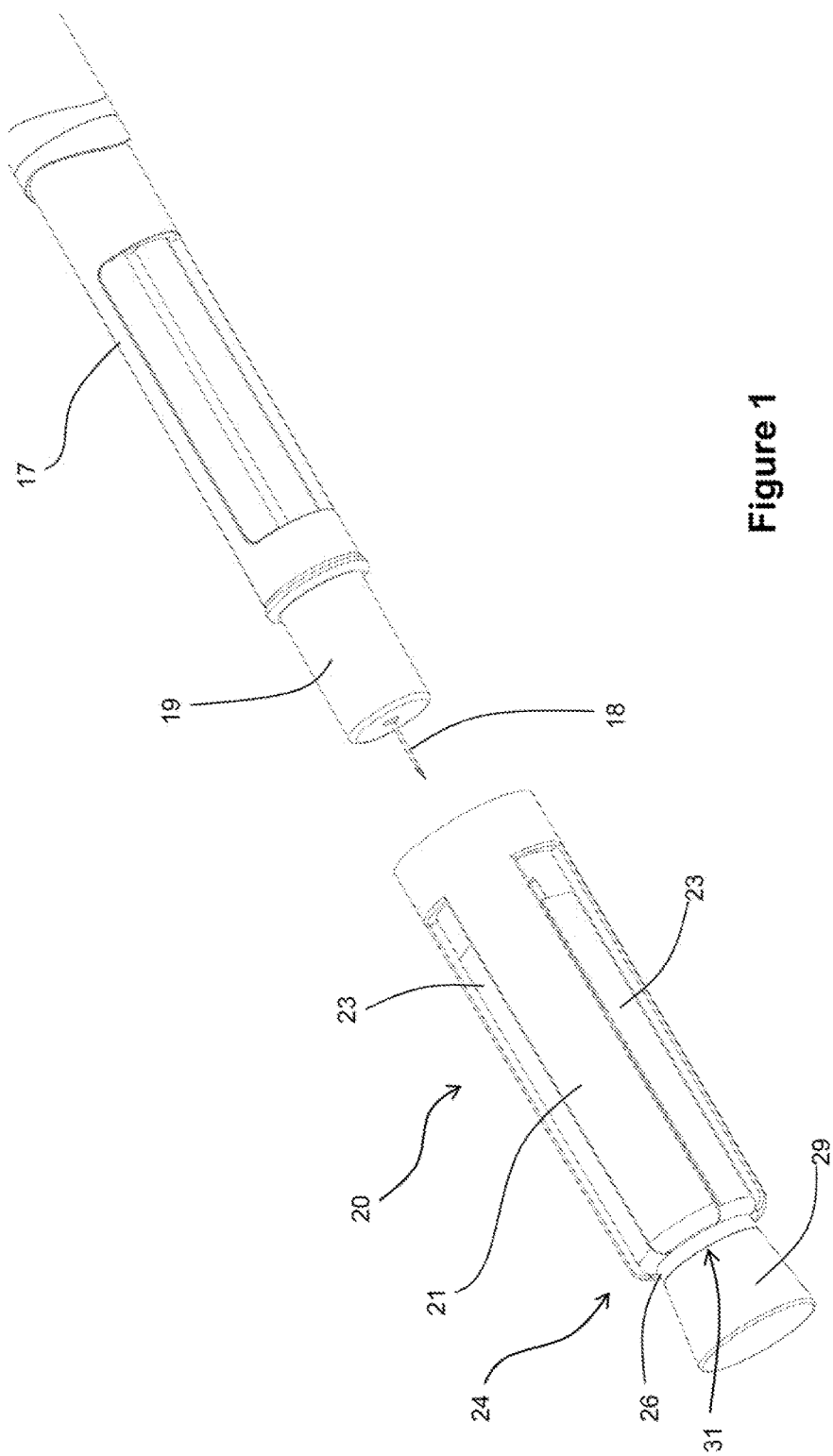
FIGS. 1 and 2 show a first embodiment of safety needle device having a soft needle cover, FIG. 1 showing the cover attached to the front face of the device sleeve and FIG. 2 showing the cover being pulled away therefrom.

Throughout the following description of the various embodiments of this invention, the same reference characters will be used to designate the same components, or essentially the same components having the same function. Wherever appropriate, once those components have been described, they will not be described again.

Figure 2:
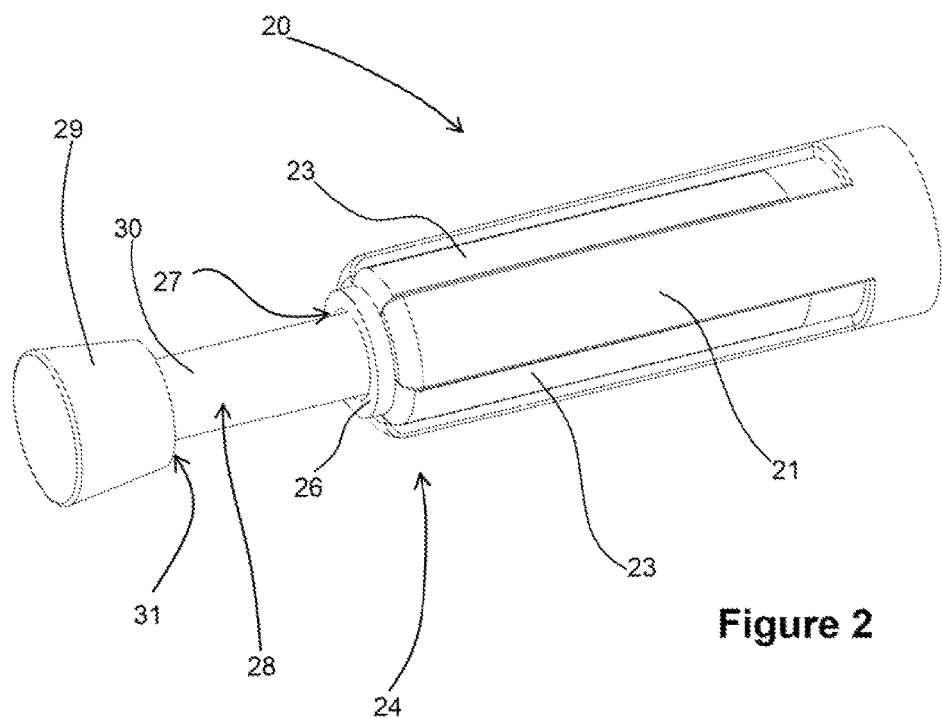

The first embodiment is shown in FIGS. 1 and 2. This comprises a safety needle device 20 generally corresponding to that shown and described in my earlier Patent Application No. 10 060789.0, to which a reference may be made for a more complete discussion. Further, a similar safety needle device is also shown in my earlier Application No. 10 01506.3 and reference may be made to that for a discussion thereof.

The safety needle device 20 has a sleeve 21 slidably mounted on a carrier (not shown) such that the sleeve may slide rearwardly over the body of a syringe (not shown) so as to expose a needle (also not shown) projecting forwardly from the syringe. Resilient (or spring) fingers 23 project rearwardly from the forward end 24 of the sleeve 21 and are resiliently deformed outwardly on rearward movement of the sleeve, to urge the sleeve back to its initial position, shown in FIGS. 1 and 2.

The forward end of the sleeve has an annular surface 26 with a central orifice 27, through which the sharp tip of the needle projects when the sleeve has been slid rearwardly with respect to the syringe, and so also the needle. Extending through that orifice is a soft (i.e. of a resilient material such as a natural or synthetic rubber) needle cover 28 which has an axial opening from its rear end for receiving the needle, the tip of the needle penetrating the material of the cover. The rear end of the cover effects a seal to the needle mount, which may be a separate needle hub, or a part of the syringe to which the needle is attached and from which the needle projects forwardly.

Externally of the sleeve, the cover 28 is provided with an enlarged head 29, in this embodiment of a frusto-conical form with the largest diameter thereof at the free end of the cover. The smallest diameter of the frusto-conical form adjoins a cylindrical part 30 of the cover, there being a shoulder 31 (FIG. 2) between that cylindrical part 30 and the head 29.

FIG. 1 shows the arrangement in its as-manufactured form, in association with an entirely conventional pen-type medical injector 17 having a threaded boss at its forward end, on to which is screwed a medical needle 18 having a hub 19. The shoulder 31 is attached to the annular surface 26 at the forward end 24 of the sleeve. An adhesive may be used to attach the shoulder 31 to the surface 26, that adhesive being sufficiently cohesive to hold the cover against accidental or inadvertent popping-off during manufacture, as described hereinbefore. The adhesive moreover ensures the surface 26 remains sterile after the manufacture of the device. Though the adhesive should be sufficiently strong for the above-mentioned purposes, it should be not so strong as to prevent the cover 28 being pulled away from the sleeve 21 by an axial force applied manually to the head 29 when the device is to be prepared for use. The head is profiled to assist the pulling of the cover, so that the cover as a whole is released from the sleeve as shown in FIG. 2, so preparing the device ready for performing a procedure.

So long as the safety device including its cover is manufactured under sterile conditions, annular surface 26 of the sleeve will remain sterile until the cover is pulled away from the sleeve, preparing the device for use. Moreover, the attachment of the cover to the sleeve allows the cylindrical part of the cover 30 to be subjected to an axial compressive force so long as that cylindrical part has a length slightly greater than the distance between the annular surface 26 of the sleeve and the part of the needle mount engaged by the cover thereby to enhance the sealing effect thereof and so the protection of the needle. Again, the bond provided by the attachment should be sufficiently strong for this purpose while still allowing the cover to be pulled away when the device is to be prepared ready for use.

As an alternative to the use of an adhesive, other attachment techniques may be employed, such as a thermal or chemical fusing operation on the abutting annular surface 26 and shoulder 31. Alternatively, a welding process may be used and in that case this may be a laser welding process, effected either externally of the sleeve and performed circularly therearound, or internally of the sleeve, on to the abutting faces. In a similar way, a laser using operation could be performed.

Yet another possibility would be to co-mould or insert-mould the cover together with the sleeve, using an appropriate mould tool and also appropriate materials for the sleeve and cover. Typically, the sleeve may be made of a polycarbonate whereas the cover may be of a thermoplastic elastomer such as of a synthetic or natural rubber. Co-moulding and insert-moulding processes are well known and understood in the plastics moulding art and will not be described in further detail here.

Figure 3:
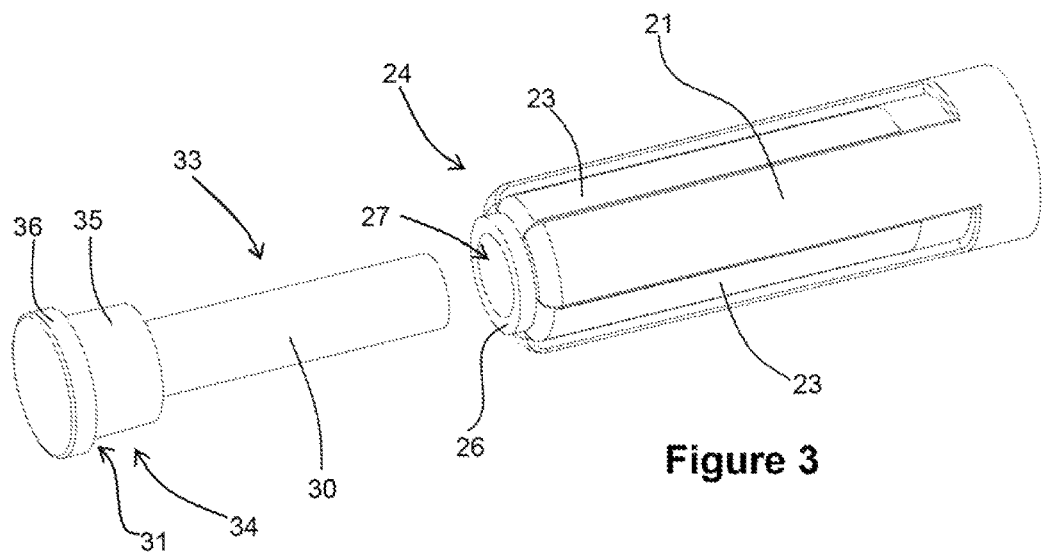
FIG. 3 shows a second embodiment having a cover profiled slightly differently from that of FIGS. 1 and 2.

FIG. 3 shows a cover 33 having a modified head 34, as compared to the embodiment of FIGS. 1 and 2. This head 34 has a cylindrical first portion 35 which provides the shoulder 31 and a second, larger cylindrical portion 36 at the free end of the head. The step between the first and second cylindrical portions assists the gripping of the head for pulling the cover away from the sleeve and also reduces the likelihood of the fingers of a user contacting the annular surface 26, in the course of that process of pulling the cover away.

Figure 4:
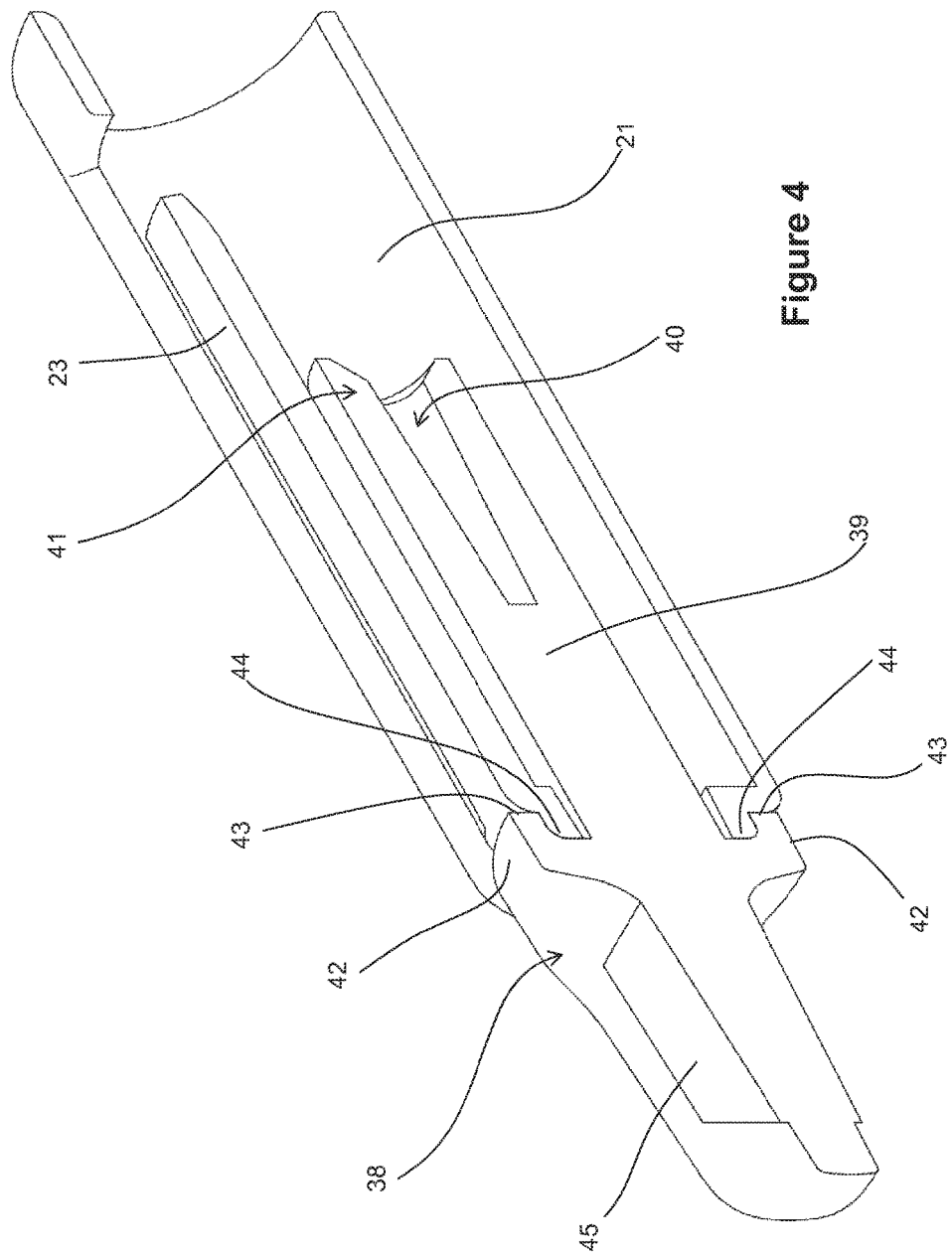
FIG. 4 is an isometric axial section through part of a safety needle device, showing the co-operating sleeve and cover, as a third embodiment.

FIG. 4 is an isometric view of an axial section the third embodiment, this having a sleeve 21 as described hereinbefore and a cover 38 including a cylindrical part 39 extending within the cover back towards the needle mount (not shown). As can be seen, this cylindrical part has an opening 40 extending forwardly from the rear end 41 of the cover, such that the needle (not shown) may extend within that opening but with the tip of the needle penetrating the material of the cover so as to be stopped thereby. In addition, the rear end 41 of the cover is profiled for effecting a seal against the needle mount.

Externally of the sleeve, the cover has a flange 42 with a lip 43 therearound so defining an annular recess in which is received a rib 44 of the sleeve. The flange 42 of the cover may be attached to the forward end of the sleeve by an adhesive or any of the other techniques discussed above, depending on the materials of the sleeve and cover. The external part of the cover provides a substantially flat tab 45 for a user to grip and pull the cover away from the sleeve. By profiling the external part of the cover in this way, contact between a user's fingers and the forward end of the sleeve is highly unlikely, when pulling the cover away from the sleeve.

Figure 5:
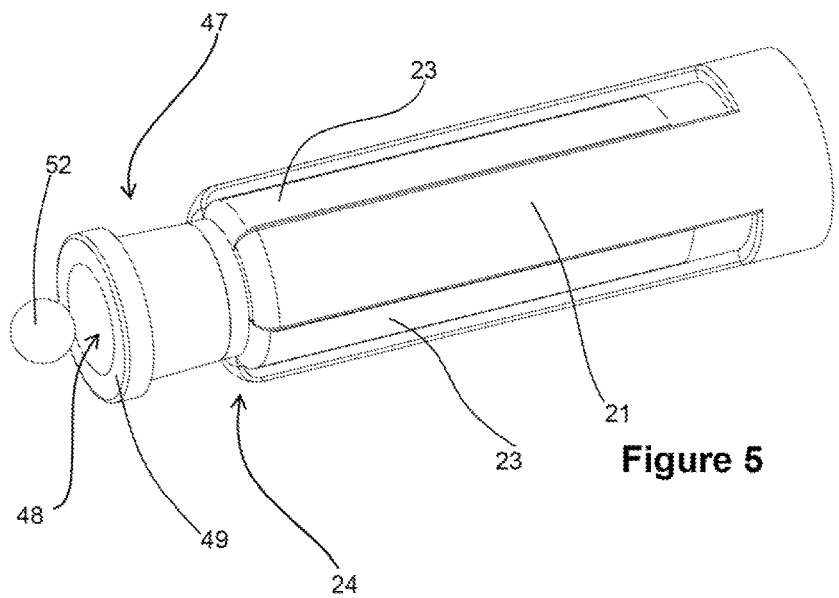
FIGS. 5 and 6 show a fourth embodiment, respectively in isometric and axial sectional views.
Figure 6:
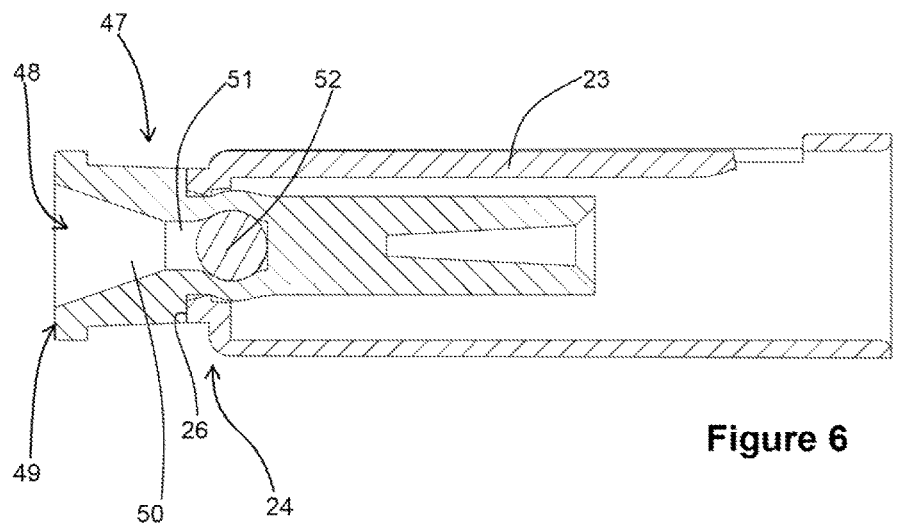

The fourth embodiment is shown in FIGS. 5 and 6. The cover 47 is similar to cover 38 of the second embodiment, but is provided with an axial opening 48 extending rearwardly from the forward end face 49 of the cover. The opening has a funnel-shaped profile 50 leading into a generally parallel bore 51 at the deepest part of the opening.

FIG. 5 shows the cover 47 fitted into the sleeve 21, with an expansion member in the form of a ball 52 about to be pressed into the opening 48. In FIG. 6, the ball is shown pushed fully into the opening, to the blind end of the bore 51. This radially expands the cover within the sleeve, immediately behind the forward end 24 thereof, so as to retain the cover within the sleeve and also to ensure that when in use, the part of the cover between the rearward end thereof and the forward end of the sleeve is in compression. This radial expansion also serves to prevent the cover popping-off during manufacture, as described above. In addition, the expansion of the cover behind the orifice at the forward end of the sleeve ensures that the external part of the head of the cover bears against the annular surface 26 of the sleeve. This ensures the annular surface may remain sterile but this may be assisted by the provision of a sealing agent such as a gel around that surface.

When the safety needle device is to be used, the head of the cover is grasped and pulled away from the sleeve, the enlarged part of the cover being compressed as necessary on passing through the orifice at the forward end of the sleeve.

Figure 7:
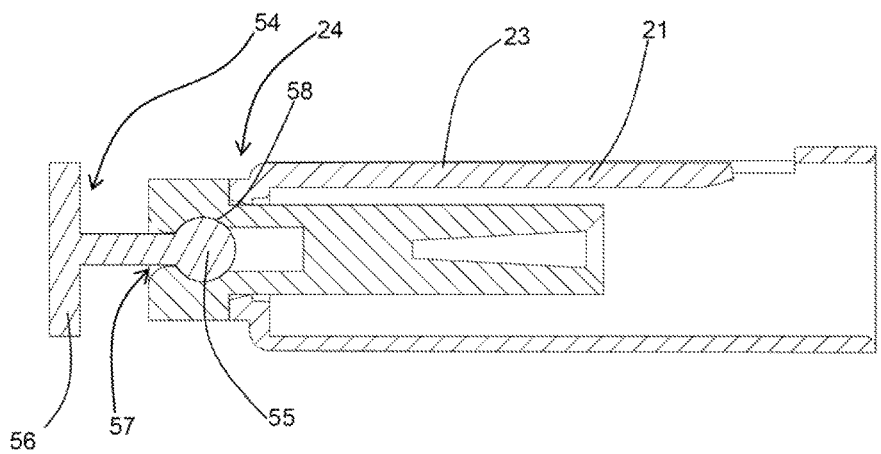
FIGS. 7, 8 and 9 are axial sections through a fifth embodiment, respectively during manufacture, subsequent to manufacture and in preparation for performing a medical procedure.
Figure 8:
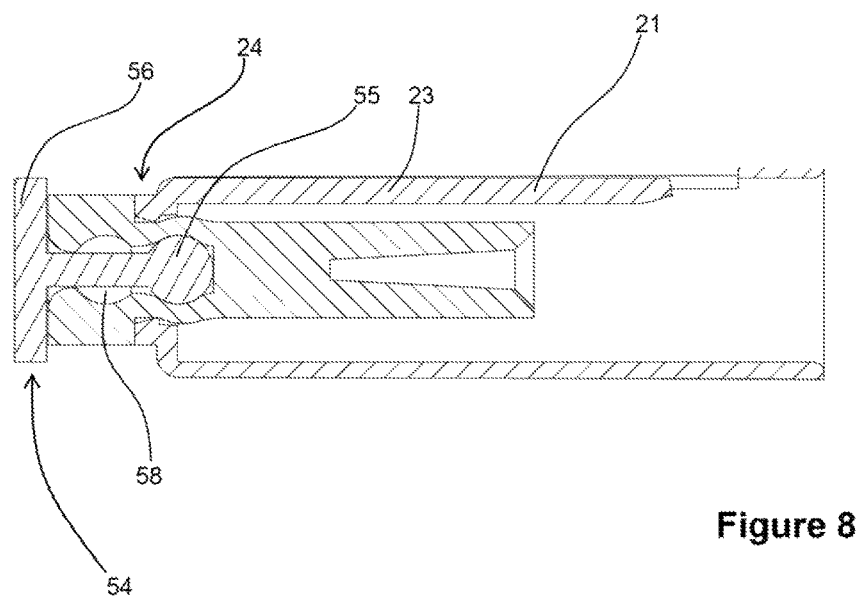
Figure 9:
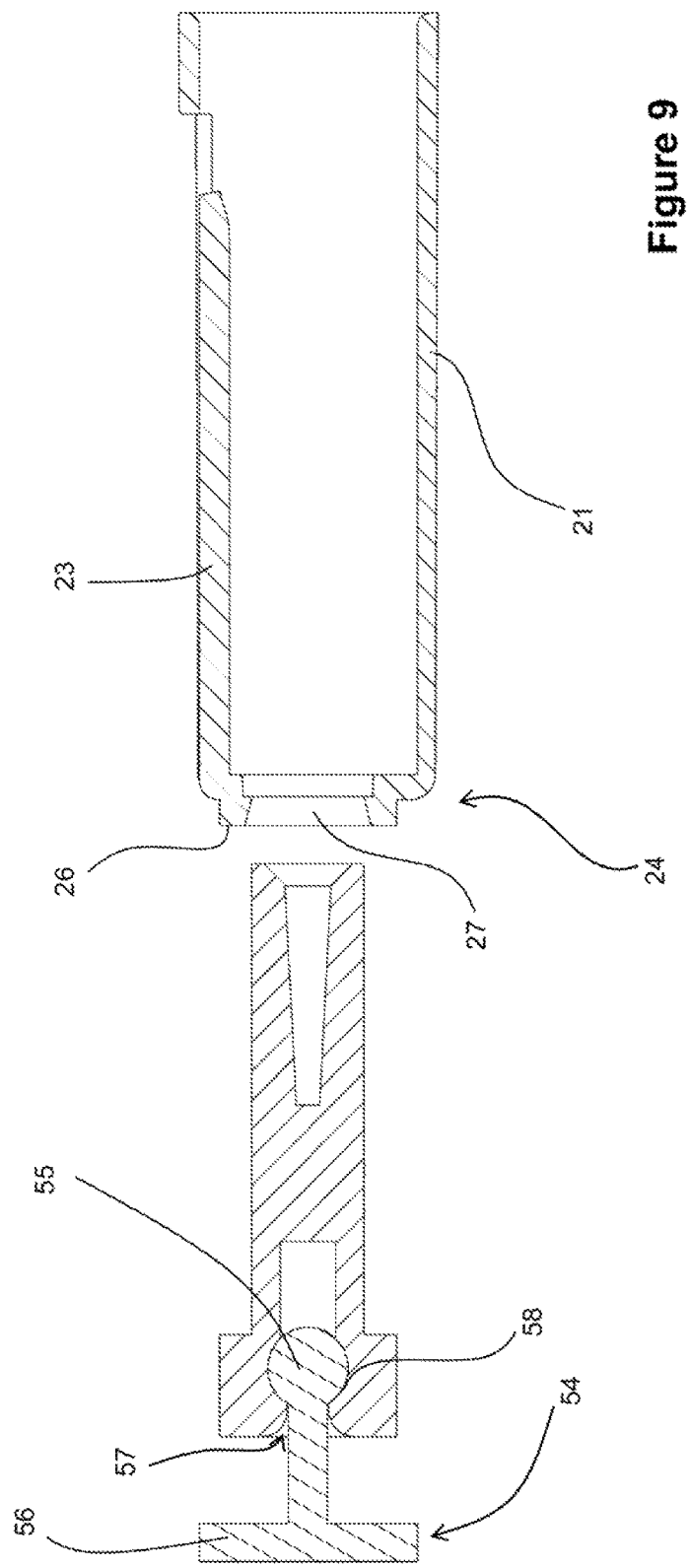

The fifth embodiment shown in FIGS. 7 to 9 operates on the same principle as the fourth embodiment but instead of employing a loose ball 52, the expansion member is in the form of a plunger 54 having a generally spherical enlarged end 55 and a flanged end 56. The profile of the opening 57 into the cover is different from that of FIGS. 5 and 6. Here, the opening has a bell-mouth leading to a groove 58 of arcuate cross-section, from which a parallel bore extends rearwardly.

As shown in FIG. 7, the cover is fitted to the sleeve 21 with the spherical end 55 of the plunger 54 located in the groove 58. As before, a sealing agent may be provided between the forward end 24 of the sleeve and the abutting surface of the cover. The plunger 54 is then pressed rearwardly such that the spherical end moves through the orifice in the sleeve, to be located behind the forward end of the sleeve and the flanged end lies against the forward end of the cover, as shown in FIG. 8. As with the previous embodiment, the cover is expanded radially within the sleeve so as to retain the cover in position, to allow the part of the cover within the sleeve to be subjected to compression and also to prevent the cover popping-off during manufacture. Moreover, a sterile seal may be provided between the cover and the external annular surface at the forward end of the sleeve.

When the safety needle device is to be prepared for use, the flanged end 56 of the plunger 54 is grasped and pulled away from the sleeve. This may bring the cover with it, as with the previous embodiment, or the plunger may move relative to the cover until the spherical end 55 is once more located in the groove 58 so allowing the cover to return to its original shape, whereafter further pulling on the plunger draws the cover out of the sleeve.

Figure 10:
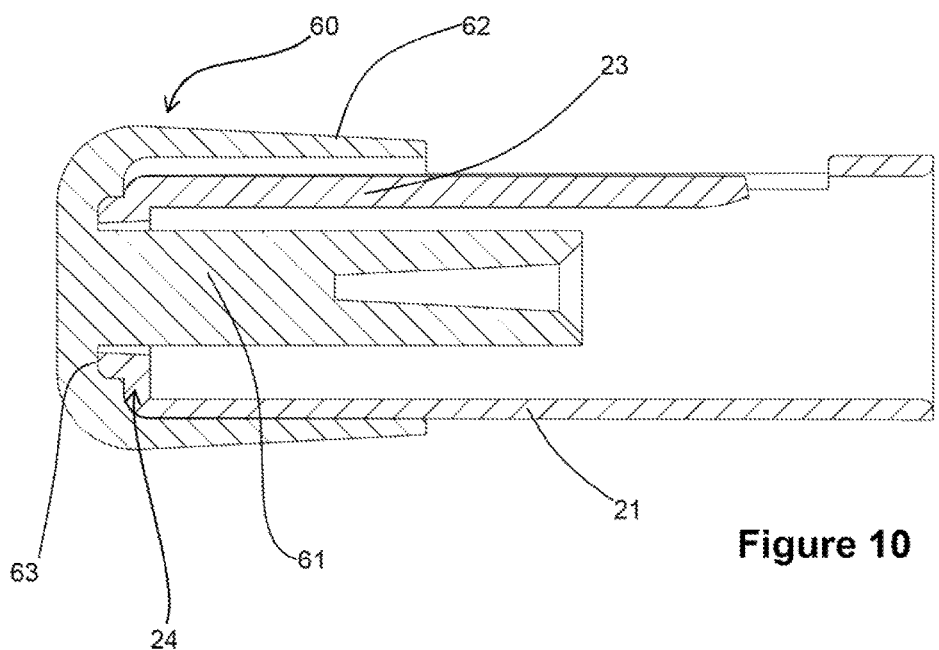
FIGS. 10 and 11 are axial sections through part of a safety needle device showing the co-operating sleeve and cover, as a sixth embodiment.
Figure 11:
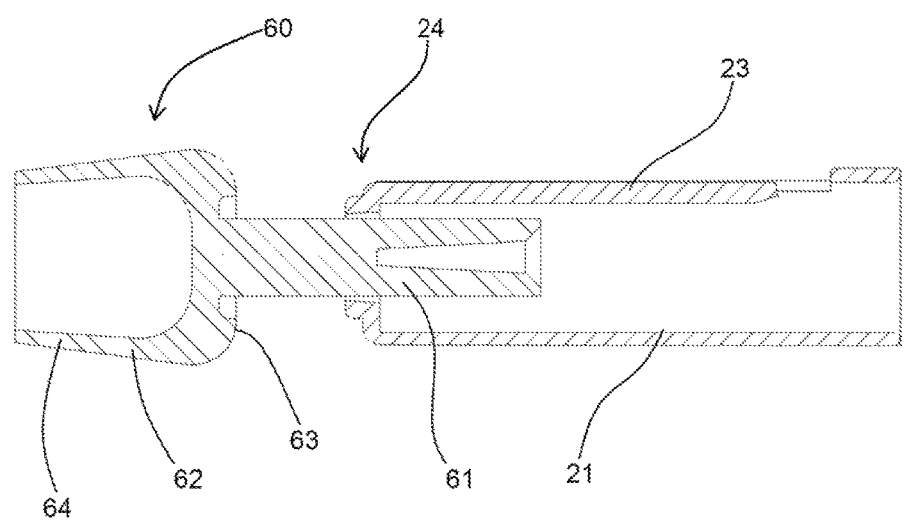
Figure 12:
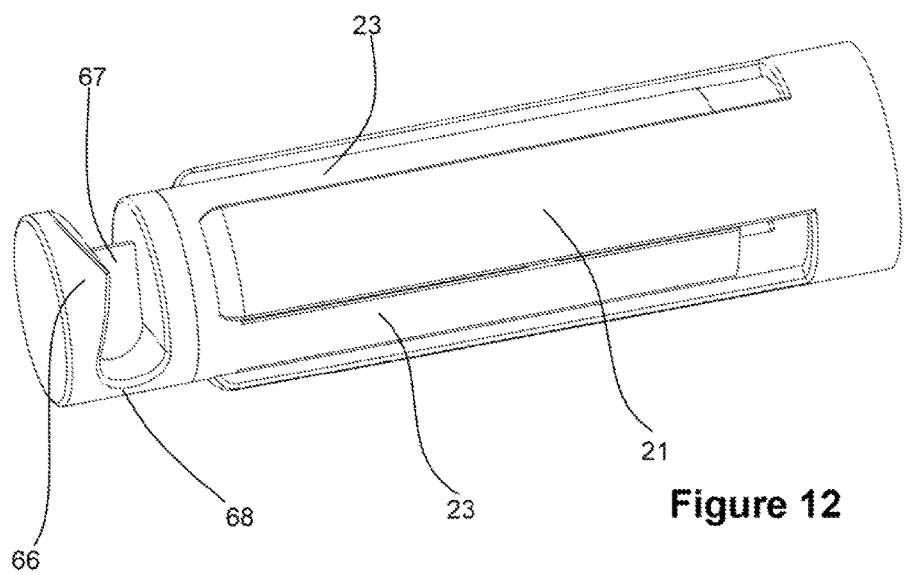
FIGS. 12 to 15 are isometric views of a seventh embodiment, having a tab for assisting the pulling away of the needle cover, from the remainder of the safety needle device.

FIGS. 10 and 11 show the sixth embodiment. The cover 60 of this embodiment is of a soft resilient synthetic rubber such as synthetic polyisoprene and has a part 61 located within the sleeve 21, in the manufactured condition of the safety needle device. Externally of the sleeve, the cover has a cylindrical part 62 which surrounds and closely fits against the external surface of the sleeve, except where there is a resilient finger 23, as shown in the upper part of FIG. 10.

Conjoining the internal and external parts 61,62 of the cover is an end portion 63 extending in a generally radial plane and which effects a seal to the forward end 24 of the sleeve. Again, a sealing agent or even an adhesive may be employed to ensure a sufficient seal is achieved here.

When the safety needle device of this embodiment is to be prepared ready for use, the external cylindrical part 62 of the cover is rolled forwardly so inverting that part of the cover to have the profile shown in FIG. 11. This then provides a grip 64 by means of which the cover, as a whole, may be withdrawn from the sleeve as shown in that Figure.

In an alternative arrangement, not shown in the drawings, the external cylindrical part of the cover may be given sufficient rigidity to prevent the inversion thereof as described above. Instead, a sealing lubricant may be applied to the internal surface of that cylindrical part or to the external surface of the sleeve. The cylindrical part should still sufficiently grip the external surface of the sleeve to hold the cover against popping-off in manufacture, and also to allow the part of the cover within the sleeve to be subjected to compression, while still allowing the cover to be drawn away from the sleeve merely by applying pressure to the rearward edge of the external part of the cover, overlying the sleeve.

FIGS. 12 to 15 show the seventh embodiment, where a cover generally corresponding to that described in relation to FIG. 3 is provided with a tab 66 to facilitate the withdrawal of the cover, from the sleeve. Apart from as will now be described, the cover corresponds to that of FIG. 3, including the attachment of the cover to the annular surface 26 of the sleeve.

Figure 13:
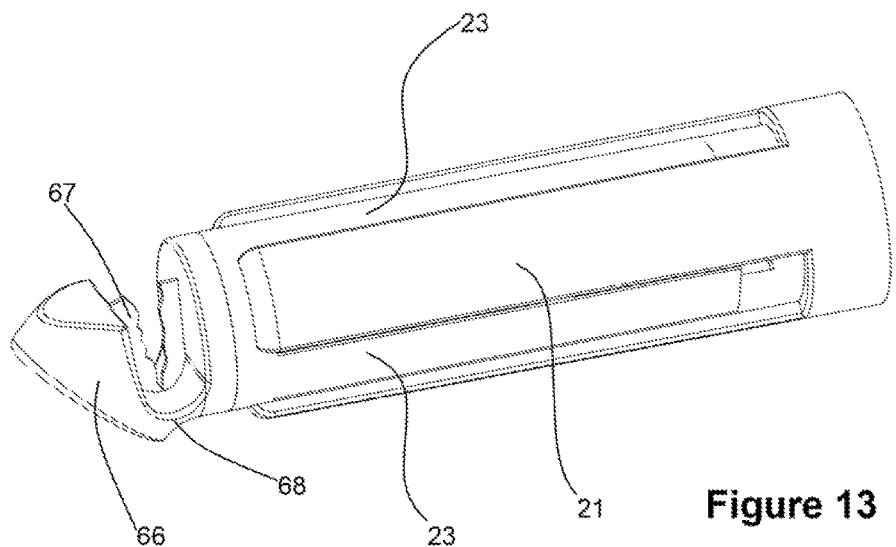

The tab 66 is moulded integrally with the remainder of the cover and is connected thereto by a relatively thin web 67, apart from at a peripheral region 68, such that the tab lies generally in a radial plane relative to the cover. When the cover is to be withdrawn, the tab 66 is pulled generally in the axial direction away from the device, so rupturing the web 67 and allowing the tab to flex about the peripheral region 68 connecting the tab to the remainder of the cover (FIG. 13).

Figure 14:
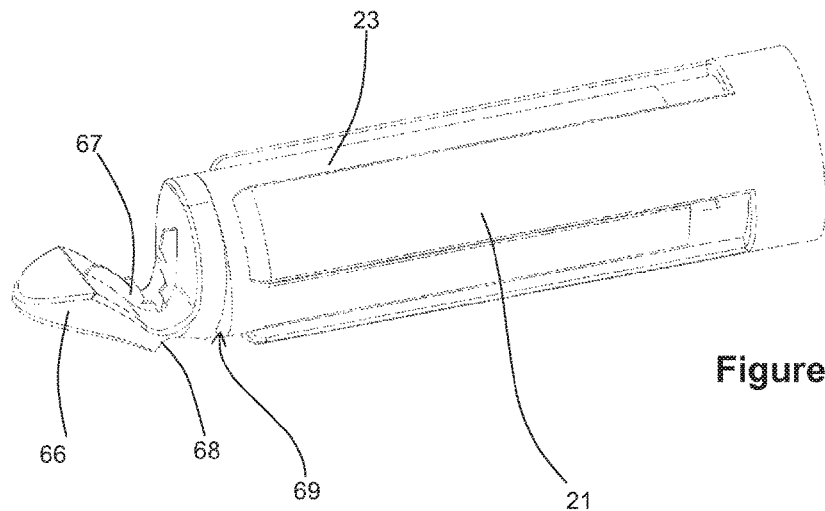
Figure 15:
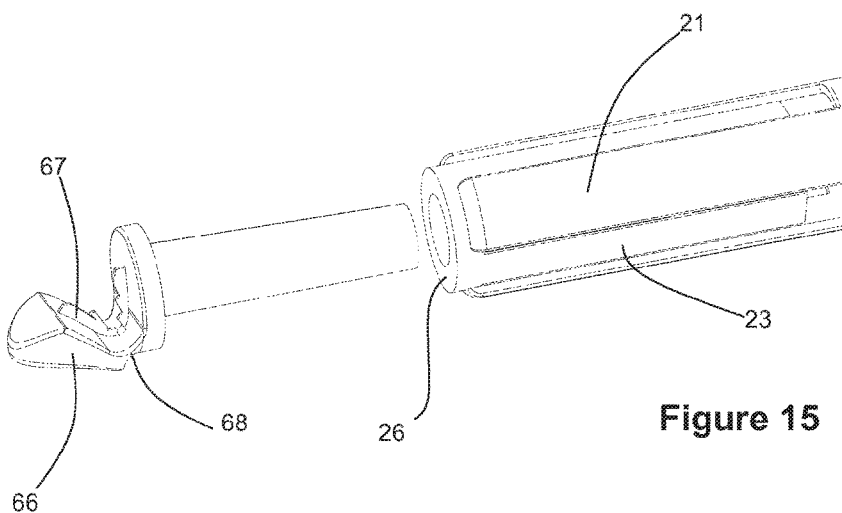

Continued pulling on the tab then flexes the part of the cover abutting the annular surface 26 of the sleeve, so gradually peeling the cover away from that peripheral surface, as shown at 69 in FIG. 14. Eventually, the entire attachment to the sleeve annular surface 26 is broken away so allowing the cover wholly to be withdrawn out of the sleeve, as shown in FIG. 15.

Figure 16:
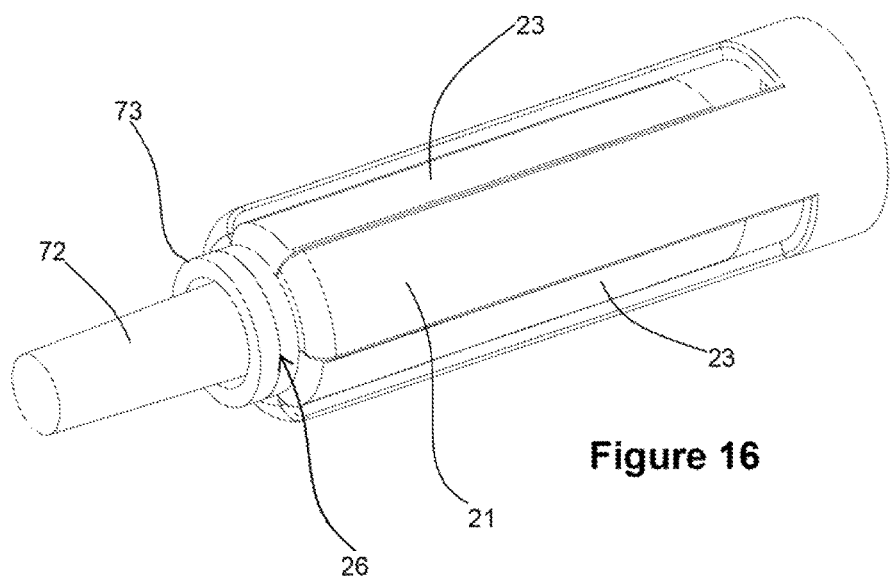
FIGS. 16 and 17 are isometric views of an eighth embodiment of cover for a safety needle device.
Figure 17:
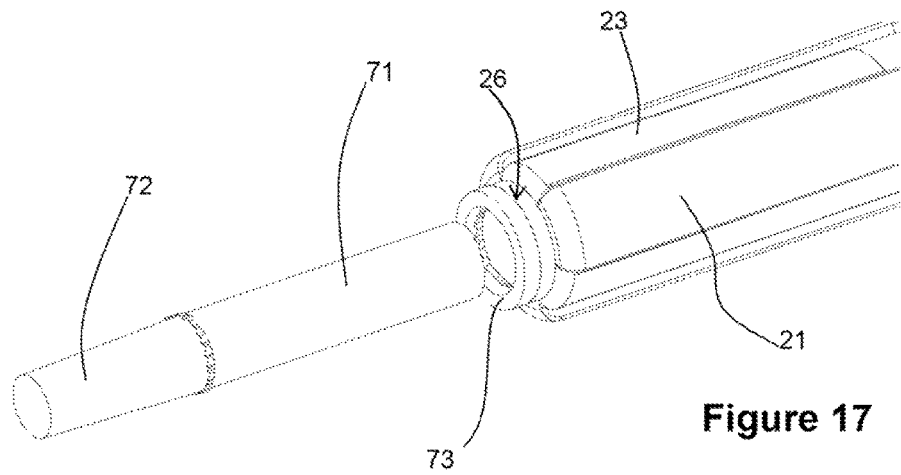

The eighth embodiment is shown in FIGS. 16 and 17 and this has the additional advantage of providing a tamper-evident property. Here, the cover has a generally cylindrical portion 71 which, as manufactured, is located within the sleeve 21 and a tapering external portion 72. A flange 73 is moulded integrally with the cover to be connected thereto by a weakened zone, around the region of the junction between the cylindrical portion 71 and external portion 72.

As manufactured, the cover is fitted to the sleeve and the abutting faces of the flange 73 and annular surface 26 of the sleeve 21 are attached to one another by any of the techniques described hereinbefore, including the use of an adhesive, a welding or fusion operation or even a co-moulding or insert-moulding process. This allows the cylindrical portion 71 within the sleeve to be under axial compression so that the rear end thereof effects a seal to the needle mount, and also to prevent the cover popping-off, during manufacture. When the device is to be used, the external portion 72 is grasped and pulled axially away from the sleeve, so severing the weakened zone between the flange 73 and the remainder of the cover (FIG. 17). When fully pulled away, the safety needle device is ready for use, with the flange 73 of the cover remaining attached to the forward end of the sleeve, so showing the cover has been pulled away and thus conferring a tamper-evident seal.

It will be appreciated that the arrangements of this invention may be combined with the various safety needle devices described in said applications, in place of the needle covers described therein. Moreover, the features of one or more of these embodiments may be combined to give rise to an advantageous needle cover. For example, the tab 66 of the seventh embodiment may be used in conjunction with other embodiments herein, or the embodiments of said applications.

The invention claimed is:

1. A safety device for a medical injector, the medical injector having a part supporting a needle, the needle having a tip and the needle projecting forwardly from said supporting part of the injector, said device comprising:
   a tubular sleeve for surrounding the needle and slidable rearwardly, in use, with respect to said needle to expose at least the tip of said needle, the sleeve having a forward end comprising an external forward facing annular end face lying in a generally radial plane relative to the sleeve, said annular end face surrounding an orifice for said needle to project through when the sleeve is slid rearwardly; and
   a removable needle cover extending through the orifice and comprising an internal portion and an external portion, the internal portion of the needle cover extending rearwardly from said end face to cover the tip of the needle and a rear end of the needle cover contacting said supporting part of the injector thereby creating, in use, a first seal to said supporting part of the injector, the external portion of the needle cover extending forwardly of said annular end face and including a radially outwardly extending shoulder extending over said annular end face;
   wherein the needle cover is attached and bonded to the tubular sleeve at said forward end of the sleeve to provide a second seal between the removable needle cover and the tubular sleeve at said annular end face, and the attachment of the needle cover to the forward end of the sleeve and the contact between the rear end of the needle cover and said supporting part of the injector prevents rearward sliding of the sleeve and, in use, said bond is breakable to separate the needle cover from the sleeve thereby exposing both said annular end face and the needle tip within the sleeve and permitting rearward sliding of the sleeve.

2. The safety device as claimed in claim 1, wherein the needle cover is bonded to the forward end of the sleeve by one of a thermal or chemical fusing, welding or a moulding operation.

3. The safety device as claimed in claim 2, wherein the needle cover is bonded to the forward end of the sleeve by a laser fusing or welding operation.

4. The safety device as claimed in claim 2, wherein the needle cover is bonded attached directly to the forward end of the sleeve by one of a co-moulding operation or an insert moulding operation.

5. The safety device as claimed in claim 1, wherein the needle cover is resiliently deformable.

6. The safety device as claimed in claim 1, wherein a forward end of the needle cover is provided with a tab connected to the needle cover by a web which holds the tab in a generally radial plane with respect to the axis of the sleeve, whereby the tab is freed for use to pull the needle cover away from the sleeve by dividing the web so allowing the tab to flex out of said generally radial plane.

7. The safety device as claimed in claim 6, wherein the web is separable by tearing with the application of a sufficient force on the tab to effect a flexing movement thereof.

8. The safety device as claimed in claim 6, wherein the tab flexes about a connection to the needle cover at one end of the tab adjacent a side wall of the needle cover and the web extends across the needle cover in a generally radial plane with respect to the axis of the sleeve.

9. The safety device as claimed in claim 8, wherein said connection of the tab to the needle cover comprises a hinge defined by a weakened zone of the material of the needle cover and the tab.

10. The safety device as claimed in claim 1, wherein:
    the part supporting the needle is a needle hub;
    an internal portion of the needle cover has a rear end for engaging said needle hub; and
    the internal portion of the needle cover is of an elastomeric material adapted to be placed under compression within the sleeve thereby effecting the first seal to the needle hub.

11. The safety device as claimed in claim 1 in combination with a needle arranged within the sleeve before the sleeve is slid rearwardly, the removable needle cover covering the tip of the needle until the needle cover is removed.

12. The safety device as claimed in claim 11, wherein the needle projects forwardly from a medical injector and the safety device co-operates with the injector.

13. The safety device as claimed in claim 1, wherein the shoulder of the needle cover abuts the annular end face of the sleeve.

14. The safety device as claimed in claim 1, wherein the shoulder of the needle cover is bonded to the annular end face of the sleeve.

15. A safety device for a medical injector, the medical injector having a part supporting a needle, the needle having a tip and the needle projecting forwardly from said supporting part of the injector, said device comprising:
    a tubular sleeve for surrounding a needle and slidable rearwardly, in use, with respect to said needle to expose at least the tip of said needle, the sleeve having a forward end comprising an external forward facing annular end face lying in a generally radial plane relative to the sleeve, said annular end face surrounding an orifice for said needle to project through when the sleeve is slid rearwardly;
    a removable needle cover extending through the orifice and comprising an internal portion and an external portion, the internal portion of the needle cover extending rearwardly from said end face to cover the tip of the needle and a rear end of the needle cover contacting said supporting part of the injector thereby creating, in use, a first seal to said supporting part of the injector, the external portion of the needle cover extending forwardly of said annular end face and including a radially outwardly extending shoulder extending over said annular end face of the sleeve, and a forward end face of the cover including an opening and an axial bore extending rearwardly from said opening; and
    an expansion member within or receivable within the axial bore, the expansion member moveable to a position in the axial bore in which the expansion member radially expands a part of the internal portion of the needle cover within the sleeve so as to retain the internal portion of the needle cover within the sleeve, wherein the internal portion of the needle cover retained within the sleeve prevents rearward sliding of the sleeve and, in use, the needle cover is separated from the sleeve by applying sufficient force to the needle cover to radially compress said expanded part of the needle cover and draw the internal portion of the needle cover forwardly through the orifice, thereby exposing both said annular end face and the needle tip within the sleeve and permitting rearward sliding of the sleeve.

16. The safety device as claimed in claim 15, wherein the expansion member is in the form of a ball.

17. The safety device as claimed in claim 15, wherein the expansion member is in the form of a plunger having an enlarged end.

18. The safety device as claimed in claim 17, wherein the plunger is moveable between a first position in which the enlarged end is in the axial bore and radially expands a part of the internal portion of the needle cover within the sleeve and a second position in which the enlarged end is in the axial bore in the external portion of the needle cover forward of the annular end face of the sleeve.

19. The safety device as claimed in claim 15, wherein the bore is a blind bore.

20. A safety device for a medical injector, the medical injector having a part supporting a needle, the needle having a tip and the needle projecting forwardly from said supporting part of the injector, said device comprising:
   a tubular sleeve for surrounding a needle and slidable rearwardly, in use, with respect to said needle to expose at least the tip of said needle, the sleeve having a forward end comprising an external forward facing annular end face lying in a generally radial plane relative to the sleeve, said annular end face surrounding an orifice for said needle to project through when the sleeve is slid rearwardly; and
   a removable needle cover extending through the orifice and comprising an internal portion and an external portion, the internal portion of the needle cover extending rearwardly from said end face to cover the tip of the needle and a rear end of the needle cover contacting said supporting part of the injector thereby creating, in use, a first seal to said supporting part of the injector, the external portion of the needle cover extending forwardly of said annular end face and including a radially outwardly extending flange and a weakened zone, a face of the flange abutting and covering said annular end face to provide a second seal between the removable needle cover and said annular end face;
   wherein the face of the flange is bonded to said annular end face such that the attachment of the flange to the end face and the contact between the rear end of the cover and said supporting part of the injector prevents rearward sliding of the sleeve and, in use, a force is applied to the needle cover to break the weakened zone to separate the flange from the remainder of the needle cover thereby permitting the internal portion of the needle cover to be drawn forwardly through the orifice thereby exposing the needle tip within the sleeve and permitting rearward sliding of the sleeve.

* * * * *